United States Patent [19]

Trott

[11] Patent Number: 5,411,522

[45] Date of Patent: May 2, 1995

[54] UNITARY ANCHOR FOR SOFT TISSUE FIXATION

[75] Inventor: Arthur F. Trott, Largo, Fla.

[73] Assignee: Linvatec Corporation, Largo, Fla.

[21] Appl. No.: 111,319

[22] Filed: Aug. 25, 1993

[51] Int. Cl.⁶ ............................................. A61B 17/04
[52] U.S. Cl. ................................ 606/232; 606/207; 606/139; 24/546
[58] Field of Search ........................ 606/232, 205–207, 606/151, 103, 139; 24/67.9, 546, 563

[56] References Cited

U.S. PATENT DOCUMENTS

| | | | |
|---|---|---|---|
| D. 275,790 | 10/1984 | Marlowe | 606/207 |
| 351,529 | 10/1886 | Schaeffer | 24/546 |
| 565,255 | 8/1896 | Belden | 24/546 |
| 884,256 | 4/1908 | Addie | 24/546 |
| 1,098,789 | 6/1914 | English | 24/67.9 |
| 1,109,967 | 9/1914 | Condon | 24/546 |
| 2,709,287 | 5/1955 | Shelton et al. | 24/546 |
| 4,041,931 | 8/1977 | Elliot et al. | 606/151 |
| 5,030,224 | 7/1991 | Wright et al. | 606/151 |

FOREIGN PATENT DOCUMENTS

| | | | |
|---|---|---|---|
| 20251 | of 1914 | United Kingdom | 606/207 |
| 853558 | 11/1960 | United Kingdom | 24/546 |

*Primary Examiner*—Gary Jackson

[57] ABSTRACT

A suture anchor includes a single length of resilient wire bent to form a suture-retaining loop disposed between two proximally diverging coplanar legs having pointed ends. The legs are selectively compressible together to permit the anchor to be inserted, loop first, into a bone tunnel having a diameter smaller than the transverse spacing between the uncompressed legs. Release of the legs inside the bone tunnel permits the pointed leg ends to penetrate the tunnel wall. An insertion tool has pivotable arms distally terminating in respective transversely extending arcuate jaws contoured to engage the anchor legs at a location adjacent the loop and compress the anchor legs upon closure of the jaws. Each jaw has one end fixed to its pivotable arm and juxtaposed with a free end of the opposing jaw. An anchor dispenser includes a plurality of storage slots for retaining respective anchors with the anchor loop radially compressed and the anchor legs diverging forwardly of the slot. Plural access bores are aligned with respective storage slots and permit the tool jaws to be inserted through a bore and directly aligned with a stored anchor. Closure of the jaws about the anchor permits the storage anchor to be removed from its slot by rotating the tool. The removed anchor can then be withdrawn through the access bore while engaged by the insertion tool, and then inserted into a bone tunnel.

17 Claims, 2 Drawing Sheets

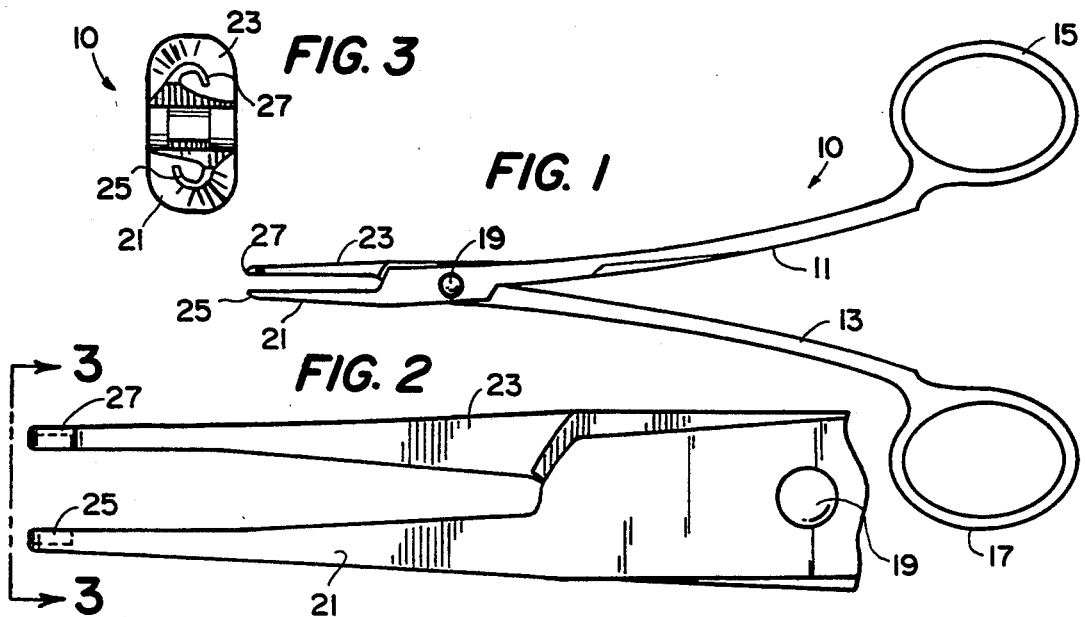
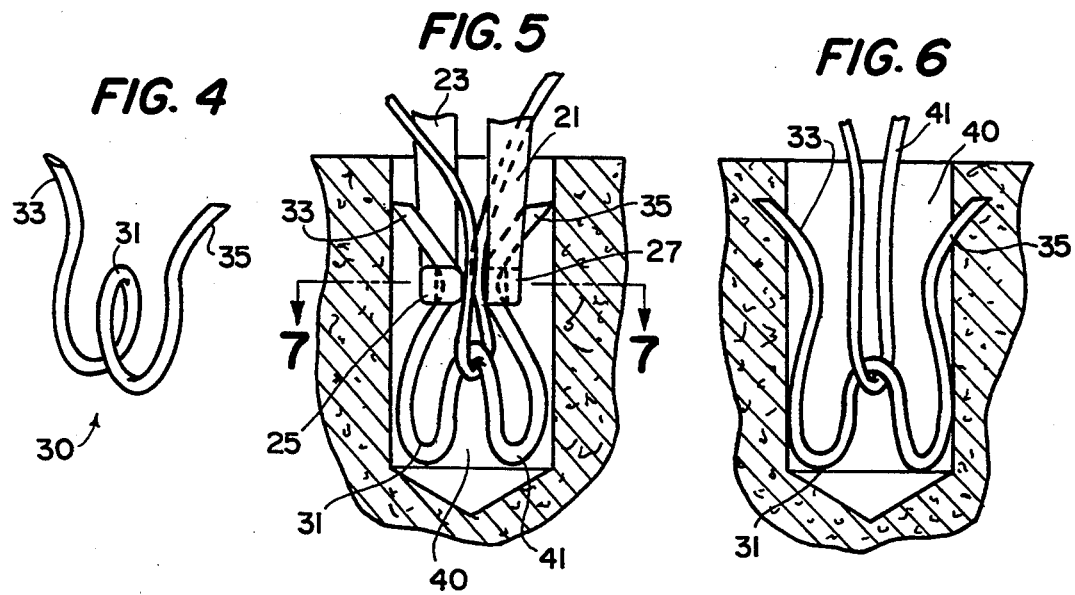
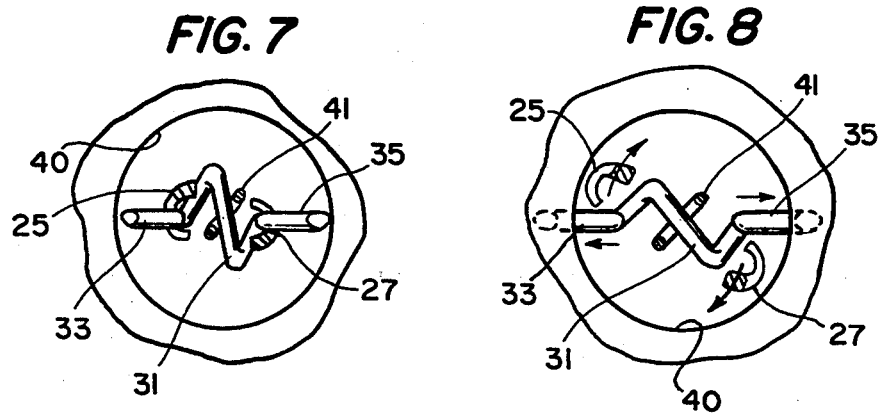

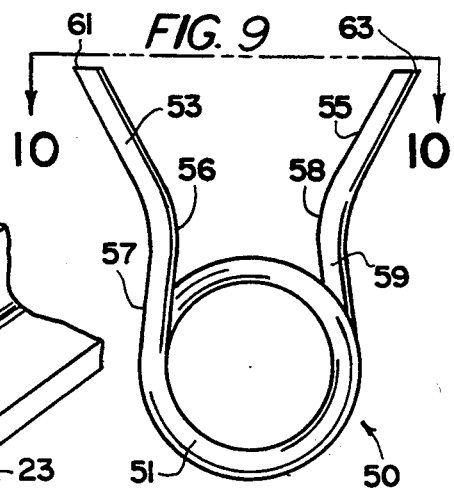
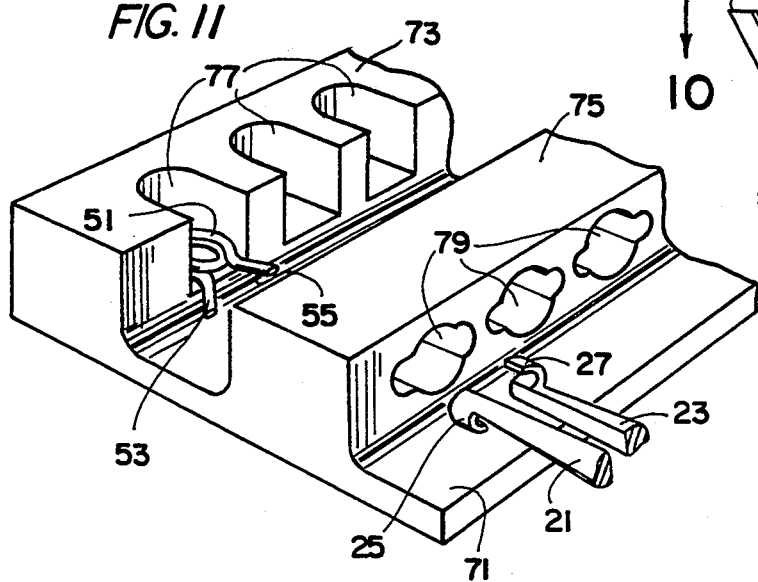
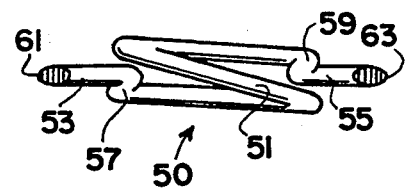
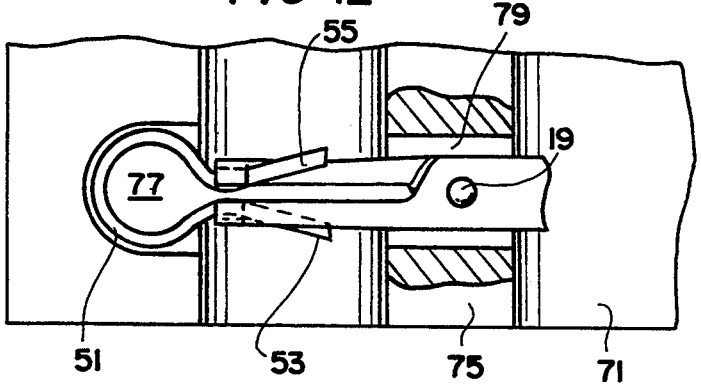

UNITARY ANCHOR FOR SOFT TISSUE FIXATION

BACKGROUND OF THE INVENTION

1. Technical Field

This invention pertains to methods and apparatus utilized in surgical procedures involving fixation of soft tissue to bone tissue and, in particular, to a novel method and apparatus for anchoring sutures to bone tissue.

2. Discussion of the Prior Art

As part of various endoscopic or arthroscopic surgical procedures it is necessary to permanently attach a suture to bone tissue. For example, in certain procedures requiring suturing of soft tissue (e.g., muscle, cartilage, tendons, ligaments, etc.) to bone tissue, the suture must be anchored to the bone tissue before suturing can proceed. The prior art includes numerous suture anchors adapted to be secured in pre-drilled holes or tunnels in the bone tissue, and most of these anchors have one or more disadvantageous characteristics. Some prior art suture anchors are required to be hammered into the bone tissue. These anchors are exemplified by U.S. Pat. Nos. 5,102,421 (Anspach, Jr.); 5,141,520 (Goble et al); and 5,100,417 (Cerier et al). Hammering, or impacting as it is often described, has the disadvantage of potential trauma and damage to surrounding bone tissue, and has limited applicability where the location of the bone tunnel is not axially aligned with an arthroscopic portal to permit transmission of the impacting force through an impactor to the anchor.

Some suture anchors are threadedly mounted in the bone tunnel, as exemplified by U.S. Pat. Nos. 5,156,616 (Meadows et al) and 4,632,100 (Somers et al). The screw insertion procedure tends to be time-consuming in that a pilot hole must first be drilled into the bone and then the hole may have to be tapped to receive the screw. If, as sometimes happens, the surgeon determines that the tunnel is not ideally located, the drilling and tapping of another pilot hole becomes necessary, thereby adding further steps to an already lengthy procedure.

Many suture anchors involve an insertion procedure wherein a relative large insertion tool must partially enter the bone tunnel along with the anchor, thereby requiring a larger diameter tunnel than would be necessary for the anchor alone. Examples of such suture anchors are found in U.S. Pat. Nos. 5,037,422 (Hayhurst et al); 4,741,330 (Hayhurst); 4,968,315 (Gatturna) and 4,899,743 (Nicholson et al). Large diameter bone tunnels for receiving suture are undesirable in many applications, particularly where the bone itself is relatively small. In addition to the insertion tool size, some anchors themselves must be so large as to limit the degree to which bone tunnel diameters can be decreased. An example of such an anchor is found in U.S. Pat. No. 5,224,946 (Hayhurst et al).

Most of the foregoing exemplar prior art suture anchors suffer from the disadvantage of being automatically permanently deployed upon insertion into the bone tunnel. Specifically, such anchors typically have permanently projecting resilient barbs, or the like, that are forced into the tunnel and engage the tunnel wall during the insertion procedure, thereby precluding any proximally directed withdrawal movement. Such withdrawal movement is precluded even if the anchor is still engaged by the insertion tool. It sometimes is desirable to fully or partially insert the suture anchor in a bone tunnel and then withdraw it while it is still engaged by the insertion tool. With most prior art anchors there is no possibility of removing the fully or partially inserted anchor; thus, a new tunnel must be drilled and a second anchor inserted. Accordingly, two (or possibly more) anchors may be left at the surgical site, only one of which is functional.

OBJECTS AND SUMMARY OF THE INVENTION

It is therefore an object of the present invention to provide improved methods and apparatus for anchoring suture to bone.

It is another object of the invention to provide a suture anchor having a very small size, thereby requiring a small bone tunnel diameter.

Another object of the invention is to provide a suture anchor capable of being temporarily inserted into a bone tunnel while engaged by a transversely small insertion tool and then easily removed or repositioned prior to actual deployment.

A further object of the present invention is to provide a suture anchor of simple resilient wire construction capable of being inserted and positively engaged in a bone tunnel with a specially configured, transversely small insertion tool.

Yet another object of the invention is to provide a method and apparatus for securing a suture anchor in a bone tunnel without requiring the tunnel diameter to be larger than necessary to accommodate the anchor.

In accordance with the present invention a suture anchor comprises a resilient wire or rod bent to form at least one complete helical loop (i.e., 360° or more) at the approximate center of the wire length to permit suture to be retained in a bone tunnel by the loop. In the preferred embodiment there are between one and a half and two such loops constituting the distal portion of the anchor. The ends of the wire are bent away from the loop to define two substantially coplanar legs extending proximally from the loop while diverging from one another. The legs are preferably straight and have pointed ends normally spaced (i.e., when unstressed) by a distance greater than the diameter of the bone tunnel in which the anchor is to be received. The bends in the legs where they join the loop define a neck location of closest transverse spacing between the anchor legs; this location serves as an engagement neck for an anchor insertion tool.

The anchor insertion tool includes a pair of pivotable arms with jaws at their distal ends. The jaws are configured to permit the engagement neck of the anchor to be selectively engaged between the jaws. With the anchor thusly engaged and the jaws closed, the legs are squeezed together at the engagement neck so that the pointed leg ends become spaced by less than the diameter of a bone tunnel. The anchor can thereby easily be inserted into the tunnel along with the insertion tool jaws. In order to deploy the inserted anchor, the insertion tool jaws are spread open and removed from the bone tunnel, thereby permitting the anchor legs to resiliently return toward their maximum spread position. The spreading coplanar anchor legs force their pointed ends into the bone tunnel wall at diametrically opposite locations in the tunnel to thereby preclude inadvertent withdrawal of the anchor. The transverse spacing between the anchor legs when engaged by the closed tool jaws permits the anchor to be moved freely into and out of the tunnel prior to actual deployment. Suture is threaded through the anchor loop before insertion of the anchor into the bone tunnel. After the insertion tool is withdrawn, the suture may be pulled to cause the pointed anchor legs to further penetrate the bone tissue.

Each tool jaw is a semi-annular member extending transversely from its tool arm with one end secured to a respective tool arm and a diametrically opposite free end. The semi-annular jaws are disposed in planes oriented perpendicular to their respective arms. The free end of each jaw is positioned opposite the secured end of the other jaw such that the jaws, when fully closed, form a complete annulus having its center disposed substantially midway between the two tool arms. Each jaw has an inner radius sized to permit that jaw to receive a respective anchor leg at the engagement location of the legs. When the jaws are opened to disengage the anchor wire within a bone tunnel, the insertion tool is manually rotated about a longitudinal axis of the tool to permit the transversely extending jaws to clear the proximally extending portions of the coplanar anchor legs as the tool is withdrawn from the tunnel.

A dispenser for the anchors includes a plurality of side by side anchor storage slots. Each storage slot has a width slightly smaller than the outside diameter of the anchor loop to enable the loop to be resiliently compressed and retained in the storage slot with the anchor legs exposed and extending through an open proximal end of the slot. Spaced proximally of the storage slot is a guide block having a plurality of side by side tool access bores, each longitudinally aligned with a respective anchor storage slot. The access bores are configured to permit insertion of the distal end of the insertion tool, with its jaws open, through the bore in an orientation that assures alignment of the jaws with the engagement neck of a stored anchor wire. With the jaws thusly aligned they may be closed to engage the anchor. The tool is then turned manually 90° to permit proximal withdrawal of the engaged anchor from its storage slot and through the access bore. The engaged anchor may then be directly inserted into a bone tunnel in a surgical procedure.

The above and still further objects, features and advantages of the present invention will become apparent upon considering the following detailed description of specific embodiments thereof, particularly when viewed in conjunction with the accompanying drawings wherein like reference numerals in the various figures are utilized to designate like components.

BRIEF DESCRIPTION OF THE DRAWINGS

FIG. 1 is a view in plan of an insertion tool configured in accordance with the present invention.

FIG. 2 is a detailed plan view of the distal end of the insertion tool of FIG. 1.

FIG. 3 is a distal end view in elevation taken along lines 3—3 of FIG. 2.

FIG. 4 is a view in perspective of an anchor wire constructed in accordance with the present invention.

FIG. 5 is a view in partial section showing the anchor wire engaged in the jaws of the insertion tool during insertion of the anchor wire into a bone tunnel.

FIG. 6 is a view in partial section showing the anchor wire in the bone tunnel after deployment.

FIG. 7 is a view in section taken along lines 7—7 of FIG. 5 and showing in detail the engagement of the anchor wire between the jaws of the insertion tool.

FIG. 8 is a view similar to FIG. 7 showing the anchor wire deployed in the bone tunnel and diagrammatically illustrating removal of the insertion tool.

FIG. 9 is a top view in plan of a second embodiment of the anchor wire of the present invention.

FIG. 10 is an end view in elevation taken along lines 10—10 of FIG. 9.

FIG. 11 is a view in perspective of an anchor wire dispenser constructed in accordance with the principles of the present invention.

FIG. 12 is a detailed view in plan and partial section of the dispenser of FIG. 11 showing an anchor wire engaged by the insertion tool and ready for removal from the dispenser.

DESCRIPTION OF THE PREFERRED EMBODIMENTS

Referring to FIGS. 1-3 of the accompanying drawings, an insertion tool 10 constructed in accordance with the present invention includes a scissors-like structure having a pair of pivotable arms subdivided into proximal arm sections 11, 13 and respective distal arm sections 21, 23. The arms are joined by a pivot 19 located closer to the distal end of the tool, thereby rendering distal arm sections 21, 23 considerably shorter than the corresponding proximal arm sections. The proximal arm sections have respective finger-receiving rings 15, 17 at their proximal ends. The distal arm sections 21, 23 have respective jaws 25, 27 extending transversely therefrom. Specifically, each jaw 25, 27 is generally semi-annular with a secured end joined to a respective distal arm section 21, 23 and a free end spaced diametrically from the secured end. Concave surfaces of jaws 25, 27 face one another, and distal arm sections 21, 23 are transversely offset such that the free end of each jaw 25, 27 is disposed opposite the secured end of the opposite jaw. Accordingly, upon closure of the insertion tool, the semi-annular jaws 25, 27 form a complete annulus centered about the longitudinal axis of the insertion tool 10. The radius of the interior surface of each jaw 25, 27 is larger than the radius of the anchor wire described below to permit the jaws to engage the anchor of the present invention.

One embodiment of the suture anchor of the present invention is illustrated in FIG. 4 and includes a resiliently flexible stainless steel wire or rod 30 bent to form at least one complete helical loop 31 located approximately at the center of the wire length. The transverse cross-section of wire 30 is circular in the preferred embodiment but may be other than circular if desired. In the illustrated embodiment the wire forms approximately one and three quarters helical loops having a relatively long helical pitch (i.e., a relatively long longitudinal distance between successive loops). The ends of the wire are bent to extend away from the loop in a common plane and constitute straight diverging legs 33, 35 having sharp pointed ends. The coplanar legs 33, 35 diverge at an angle on the order of 45° in the illustrated embodiment and, when unconstrained, have their pointed ends spaced by a distance that is greater than the diameter of the bone tunnel in which the anchor is to be deployed. When the anchor is in use, loop 30 constitutes its distal end, and the points of legs 33, 35 define its proximal end.

As illustrated in FIGS. 5 and 7, the insertion tool jaws 25, 27 have their interior surfaces contoured to engage respective anchor legs 33, 35 at an engagement neck. The engagement neck is disposed at the point of closest transverse spacing between the legs as they begin to diverge and bend away from helical loops 31. When the jaws 25, 27 of the insertion tool are closed about the engagement neck, legs 33, 35 are resiliently compressed toward one another. In the fully compressed position of the legs their pointed ends are separated by less than the diameter of bone tunnel 40, thereby permitting the insertion tool jaws 25, 27 and the engaged anchor 30 to be freely moved longitudinally and rotatably within the tunnel. Before the anchor wire is inserted into the bone tunnel 40, a suture 41 is threaded through loop 31 with the suture ends extending proximally. The suture is thus engaged by the loop and trapped by the loop in the bone tunnel. When the engaged anchor is positioned as desired in the bone tunnel, jaws 25, 27 are opened, permitting legs 33, 35 to resiliently return to their maximally spaced positions. As the legs spread their pointed ends penetrate the tunnel wall of cancellous bone-tissue at diametrically opposed locations in the tunnel to permanently deploy the anchor with the suture 41 threaded about the anchor loop.

The open insertion tool jaws can be removed from the bone tunnel 40 by rotating the insertion tool approximately 90° about its longitudinal axis as best illustrated in FIG. 8. This rotation is necessary to permit transversely extending jaws 25, 27 to clear the transversely spread legs 33, 35 of the anchor as the jaws are withdrawn from the tunnel. Once the jaws have been withdrawn, the exposed suture 41 can be pulled proximally, thereby creating tension in the suture to force the pointed ends of the anchor legs 33, 35 more deeply into the bone tunnel wall. With the anchor legs thusly penetrating the wall of tunnel 40, as best illustrated in FIG. 6, the suture can then be used to secure soft tissue, or the like against the bone tissue at the bone tunnel entrance.

It will be appreciated that the wire 30 forming the anchor must have sufficient rigidity and resistance to bending to permit the anchor legs to penetrate the cancellous tissue surrounding the tunnel. In addition, it is important that the wire have sufficient resilience to permit the legs to be resiliently brought together at the engagement neck when the anchor is engaged by the insertion tool.

In the suture anchor embodiment illustrated in FIG. 4, the helix 31 has a relatively large pitch (i.e., a large longitudinal spacing between successive loops). Typically, this configuration is obtain by providing a series of compound 180° bends to approximate the helical configuration. Such compound 180° bends allow large bend radii, resulting in lower material fatigue. It is possible, and for most cases preferable, however, to provide the helical loops with a much smaller pitch. It is much easier to manufacture a helix having a smaller pitch, and it is less likely for such a helix to have regions of critical stress. In other words, a more tightly wound helix tends to be more resistant to bending and deformation in response to tension on the suture. An example of a small pitch suture anchor of the present invention is illustrated in FIGS. 9 and 10. Specifically, anchor 50 is formed from a wire or rod of stainless steel or the like. The anchor has a helix 51 of one and one-half loops at the middle of the wire length. The anchor legs 53, 55 extend from the opposite ends of the helix at locations that are substantially diametrically opposed (i.e., locations that are spaced approximately 180° about the helix). Legs 53, 55 have respective transition segments 57, 59 extending directly from the helix and bending toward and into a common plane oriented perpendicular to the helix axis at substantially the midpoint of the helix length. The projections of the transition segments 57, 59 in this common plane are parallel or slightly converging. Upon reaching the common plane, legs 53, 55 are bent at 56, 58 respectively, to diverge at an angle which, in the preferred embodiment, is on the order of 45°. The ends of legs 53, 55 are cut on a bias to define respective outwardly directed points 61, 63. Bends 56, 58 in legs 53, 55 are the locations of closest transverse spacing between the legs and define the engagement neck for insertion tool 10.

By way of example only, anchor 50 may have the following specifications and dimensions: the wire is 316LVM stainless steel wire with a diameter of 0.020 inches; transition sections 57, 59 depart from the helix at opposite 180° locations and have lengths of 0.095 inch; bends 56, 58 have a radius of 0.010 inch; the angle between the diverging segments of legs 53, 55 is 45°; each diverging segment of legs 53, 55 is 0.095 inch in length; the overall longitudinal dimension of the anchor from points 61, 63 to the distal most part of helix 51 is 0.240 inch; the total axial length of helix 51 is 0.070 inch.

A dispenser 70 for anchors 30 or 50 is illustrated at FIGS. 11 and 12. In particular, the dispenser is preferably molded as a plastic member and includes a flat base or platform 71 having a storage block 73 and a longitudinally spaced access block 75 raised from its top surface. Storage block 73 is preferably disposed at one end of the base 71 and has plural side by side storage slots 77 defined therein. Each storage slot 77 is open to the top surface of block 73 and has an open proximal end facing access block 75. Each slot 77 has parallel side walls terminating in an arcuate distal end wall. The spacing between the side walls is slightly less than the diameter of the helix 31, 51 in anchors 30, 50, respectively, to permit each slot 77 to diametrically compress the helix of an anchor disposed within the slot. In this manner, an anchor can be resiliently engaged in a storage slot 77 with its legs 33, 35 or 53, 55 extending proximally out through the proximal opening in the slot and toward the access block 75. The bottoms of slots 77 are raised slightly from base 71 to provide access for the jaws 25, 27 of insertion tool 10 about the legs of the anchor without interference from base 71.

Access block 75 has a plurality of access bores 79 defined longitudinally therethrough, each access bore being longitudinally aligned with a respective storage slot 77 in storage block 73. Each access bore 79 is generally cylindrical with a pair of diametrically opposed channels 81 of smaller radius defined in horizontally opposite sides of the bore. Channels 81 are longitudinally coextensive with their bores 79 and extend entirely through access block 75. Access bores 78 are positioned to permit insertion tool 10 to be extended longitudinally therethrough with both its jaws 25, 27 open and passing through respective channels 81. When the insertion tool jaws reach the proximal wall of storage block 73, the jaws are positioned, by virtue of their orientation in access bore 79, to be closed upon and engage the anchor by squeezing the anchor engagement neck. Once the anchor is engaged, the insertion tool is rotated 90° to thereby similarly rotate the anchor in storage slot 77. The anchor is thereby disengaged from the storage slot and can be withdrawn from slot 77 and through access bore 79 along with jaws 25, 27. Upon removal from its dispenser, the anchor remains engaged by the insertion tool and is ready to be directly inserted into a bone tunnel in the manner described above.

The method of deploying a suture anchor in accordance with the present invention involves the following steps. First, the anchor is grasped at its engagement neck to compress its legs. This may be done with the anchor stored in the dispenser illustrated in FIGS. 11 and 12 or with the anchor positioned freely on a surface. Suture is then extended through the anchor helix and the anchor is inserted, engaged by the insertion tool, into a predrilled bone tunnel. After the anchor has been properly positioned in the tunnel, the jaws 25, 27 of the insertion tool are opened to allow the legs of the anchor to expand. Insertion tool 10 is then rotated 90° to permit jaws 25, 27 to clear the anchor legs, and the insertion tool is removed from the bone tunnel and the surgical site. Finally, tension is applied to the engaged suture to pull the anchor in a proximal direction and thereby cause the pointed ends of the anchor legs to penetrate more deeply into the bone tunnel wall.

The foregoing presumes a necessary condition, namely that the length of the anchor, from the distal end of the helix to the pointed ends of the legs, is shorter than the longitudinal depth of the bone tunnel.

It will be appreciated that the suture anchor of the present invention requires resilience or flexibility for the purpose of installation and proper functioning of the anchor. Specifically, the anchor legs must be resiliently compressible by the insertion tool jaws during anchor insertion, and then resiliently expandable upon relaxation of the jaws to firmly penetrate and engage the bone tunnel wall.

Although stainless steel has been specified as the preferred material for anchors 30 and 50 described above, the anchor may also be made of plastic, polymers (either resorbable or non-resorbable), bioceramics, ceramics and other suitable materials.

From the foregoing description it will be appreciated that the invention makes available a novel method and apparatus for anchoring suture to bone, and includes a novel suture anchor, a novel anchor insertion tool and a novel method of insertion of the suture anchor.

Having described preferred embodiments of a new and improved unitary anchor for soft tissue fixation in accordance with the present invention, it is believed that other modifications, variations and changes will be suggested to persons skilled in the art in view of the teachings set forth herein. Accordingly, it is to be understood that all such variations, modifications and changes are believed to fall within the scope of the present invention as defined by the appended claims.

What is claimed is:

1. An anchor for attaching suture in a bone tunnel having a predetermined longitudinal depth and a predetermined diameter, said anchor comprising:

a continuous wire-like member bent to form a generally helical segment of at least one complete suture-retaining loop and first and second diverging coplanar legs extending from said helical segment, said helical segment having a diameter smaller than said predetermined diameter, said first and second legs having pointed ends normally spaced by a distance greater than the predetermined diameter of said bone tunnel, said legs being resiliently compressible toward one another sufficiently to permit selective reduction of the transverse spacing between said pointed ends to at most equal said predetermined diameter, said anchor being adapted for insertion distally into said bone tunnel with said helical segment preceding said legs and said legs compressed, and wherein the overall length of said anchor from the distal end of said helical segment to said pointed ends is less than said predetermined longitudinal depth of said bone tunnel;

wherein said helical segment comprises at least one and one-half loops, and wherein said legs adjacent their points of departure from the helical segment are bent into a common plane and define a location of closest transverse spacing between the legs, said location defining the onset of divergence between said legs in a direction proximally of the anchor; and wherein said location of closest transverse spacing defines an engagement neck adjacent said helical segment.

2. The anchor of claim 1 in combination with an insertion tool having selectively openable and a closeable first and second jaws configured, when closed, to engage said engagement neck of said anchor while resiliently compressing said anchor legs toward one another.

3. The combination of claim 2 wherein said insertion tool includes first and a second pivotably engaged arms having distal ends, and wherein said first and second jaws are arcuate members extending transversely from said first and second arms, respectively, each jaw having a secured end attached to its respective arm and a free end, wherein said first and second jaws have concave surfaces facing one another and having a greater radius of curvature than said anchor legs at said engagement neck to permit said jaws to engage said neck and compress said legs together when said jaws are closed.

4. The combination of claim 3 further comprising:
a support surface;
a storage block disposed on said support surface and having a plurality of side by side anchor storage slots defined therein, each storage slot having sidewalls positioned to resiliently radially compress and hold the helical segment of said anchor, said storage slot having an open proximal end through which said anchor legs extend and diverge proximally when said helical segment is compressed and held in the storage slot; and
an access block disposed on said support surface proximally of said storage block and having a plurality of side by side access bores defined longitudinally therethrough, each access bore being longitudinally aligned with a respect storage slot and contoured to permit the open jaws of said insertion tool to be inserted distally through an access bore and have its jaws aligned with said engagement neck, and to permit an anchor engaged by closed jaws of said insertion tool to be pulled proximally through the access bore.

5. The combination of claim 3 wherein said jaws are semi-annular and a said arms of said insertion tool are positioned such that the free end of each of said jaws is transversely aligned with the secured end of the other of said jaws when said jaws are closed.

6. An anchor for attaching suture in a bone tunnel having a predetermined longitudinal depth and a predetermined diameter, said anchor comprising:
a continuous wire-like member bent to form a generally helical segment of at least one complete suture-retaining loop and first and second diverging coplanar legs extending from said helical segment, said helical segment having a diameter smaller than said predetermined diameter, said first and second legs having pointed ends normally spaced by a distance greater than the predetermined diameter of said bone tunnel, said legs being resiliently compressible toward one another sufficiently to permit selective reduction of the transverse spacing between said pointed ends to at most equal said predetermined diameter, said anchor being adapted for insertion distally into said bone tunnel with said helical segment preceding said legs and said legs compressed, and wherein the overall length of said anchor from the distal end of said helical segment to said pointed ends is less than said predetermined known longitudinal depth of said bone tunnel;

wherein said legs, adjacent their points of departure from said helical segment, are bent to define a common, plane, said legs having a engagement neck defining a point of closest transverse spacing between said legs and adjacent said helical segment.

7. The anchor of claim 6 in combination with an insertion tool having selectively openable and closeable first and a second jaws configured, when closed, to engage said engagement neck of said anchor while resiliently compressing said anchor legs toward one another.

8. The combination of claim 7 wherein said jaws are said semi-annular and a said arms of said insertion tool are positioned such that the free end of each of said jaws is transversely aligned with the secured end of the other of said jaws when said jaws are closed.

9. The combination of claim 6 wherein said insertion tool includes first and a second pivotably engaged arms having distal ends, and wherein said first and second jaws are arcuate members extending transversely from said first and second arms, respectively, each jaw having a secured end attached to its respective arm and a free end, wherein said first and second jaws have concave surfaces facing one another and having a greater radius of curvature than said anchor legs at said engagement neck to permit said jaws to engage said neck and compress said legs together when said jaws are closed.

10. A suture anchor having distal and proximal ends and configured to attaching suture in a bone tunnel having a predetermined longitudinal depth and a predetermined diameter, said suture anchor comprising:

a continuous resiliently flexible wire-like member bent to form at least one complete suture-retaining loop at said distal end and first and second diverging legs extending proximally from said loop in a common plane, said loop having a diameter smaller than said predetermined diameter, said first and second legs having pointed ends defining said proximal end of said anchor, said legs when unstressed being spaced by a distance greater than the predetermined diameter of said bone tunnel, said legs being resiliently compressible in said common plane toward one another to an extent sufficient to permit selective reduction of the transverse spacing between said pointed ends to less than said predetermined diameter, said anchor being adapted for distally directed insertion into said bone tunnel with said loop preceding said legs and said legs compressed toward one another in said common plane, and wherein the overall length of said anchor from said distal end to said proximal end is less than said predetermined longitudinal depth of said bone tunnel;

wherein the location of closest transverse spacing between said legs is adjacent said loop and defines an engagement neck adapted to be engaged and compressed between closeable concave jaws of an insertion tool.

11. The suture anchor of claim 10 wherein said loop is part of a generally helical segment of said wire-like member.

12. An insertion tool for a resilient suture anchor comprising:

selectively openable and closeable first and second jaws configured when closed to engage respective first and second transversely spaced sections of said anchor while resiliently compressing said anchor; and first and second pivotably engaged arms having distal ends wherein said first and second jaws are arcuate members extending transversely from said first and second arms, respectively, each jaw having a secured end attached to its respective arm and a free end, wherein said first and second jaws have concave surfaces facing one another.

13. The insertion tool of claim 12 wherein said jaws are semi-annular and a said arms of said insertion tool are positioned such that the free end of each of said jaws is transversely aligned with the second end of the other of said jaws when said jaws are closed.

14. A method for inserting a suture anchor into a bone tunnel comprising the steps of:

(a) engaging and resiliently compressing together a pair of diverging legs of said anchor;

(b) inserting suture into a suture-retaining section of said anchor disposed between said diverging legs;

(c) inserting the engaged anchor, suture-retaining section first, into the bone tunnel with the anchor legs diverging from said suture-retaining section and with pointed ends of said anchor legs transversely spaced by a distance smaller than the diameter of the bone tunnel; and (d) after positioning the engaged anchor in the bone tunnel, releasing said anchor to permit said anchor legs to resiliently return toward an unconstrained spread position wherein said pointed ends are spaced by a distance greater than the diameter of the bone tunnel to thereby cause said pointed ends to penetrate the wall of said bone tunnel.

15. The method of claim 14 further comprising the step of applying tension to the retained suture after releasing said anchor to cause the pointed ends of the anchor legs to further penetrate the bone tunnel wall.

16. The method of claim 14 wherein step (a) includes engaging said legs of an anchor that is resiliently retained in a dispenser where suture anchors are stored for dispensing.

17. The method of claim 14 wherein step (a) includes engaging said diverging legs between a pair of selectively closeable jaws of an insertion tool, said jaws extending transversely from respective arms of said tool, said method further comprising the steps of rotating said insertion tool about a longitudinal axis after step (d) to permit said jaws to be withdrawn from said bone tunnel without interference from said anchor legs, and then withdrawing said insertion tool from the bone tunnel.

* * * * *